US009242229B2

(12) United States Patent
Koranne et al.

(10) Patent No.: US 9,242,229 B2
(45) Date of Patent: Jan. 26, 2016

(54) FISCHER-TROPSCH CATALYSTS

(75) Inventors: Manoj M. Koranne, Clarksville, MD (US); Erling Rytter, Trondheim (NO); Sigrid Eri, Ranheim (NO); Oyvind Borg, Trondheim (NO)

(73) Assignee: GTL.F1 AG, Zurich (CH)

( * ) Notice: Subject to any disclaimer, the term of this patent is extended or adjusted under 35 U.S.C. 154(b) by 422 days.

(21) Appl. No.: 13/814,905

(22) PCT Filed: Jul. 29, 2011

(86) PCT No.: PCT/GB2011/001149
§ 371 (c)(1),
(2), (4) Date: Apr. 19, 2013

(87) PCT Pub. No.: WO2012/020210
PCT Pub. Date: Feb. 16, 2012

(65) Prior Publication Data
US 2013/0199966 A1 Aug. 8, 2013

Related U.S. Application Data

(60) Provisional application No. 61/371,912, filed on Aug. 9, 2010.

(51) Int. Cl.
*B01J 23/75* (2006.01)
*B01J 23/889* (2006.01)
*B01J 23/00* (2006.01)
*B01J 23/89* (2006.01)
*B01J 35/10* (2006.01)
*B01J 37/02* (2006.01)
*B01J 37/08* (2006.01)
*B01J 37/18* (2006.01)
*C10G 2/00* (2006.01)
*C10G 45/58* (2006.01)
*C10G 47/00* (2006.01)
*C07C 1/04* (2006.01)
*B01J 23/755* (2006.01)
*B01J 23/76* (2006.01)
*B01J 23/80* (2006.01)

(52) U.S. Cl.
CPC ............ *B01J 23/8896* (2013.01); *B01J 23/005* (2013.01); *B01J 23/75* (2013.01); *B01J 23/8913* (2013.01); *B01J 35/1014* (2013.01); *B01J 35/1038* (2013.01); *B01J 37/0201* (2013.01); *B01J 37/088* (2013.01); *B01J 37/18* (2013.01); *C07C 1/0445* (2013.01); *C10G 2/33* (2013.01); *C10G 2/332* (2013.01); *C10G 2/342* (2013.01); *C10G 45/58* (2013.01); *C10G 47/00* (2013.01); *C10G 2300/1022* (2013.01); *C10G 2300/703* (2013.01)

(58) Field of Classification Search
CPC ........ B01J 23/005; B01J 23/007; B01J 23/75; B01J 23/755; B01J 23/76; B01J 23/80; B01J 23/889; B01J 23/8896
See application file for complete search history.

(56) References Cited

U.S. PATENT DOCUMENTS

| 1,746,464 | A | 2/1930 | Fischer et al. |
| 2,102,851 | A | 12/1937 | La Brie |
| 2,548,159 | A | 4/1951 | Houtman et al. |
| 2,666,756 | A | 1/1954 | Thomas et al. |
| 2,830,877 | A | 4/1958 | Appell |
| 2,916,356 | A | 12/1959 | Keith et al. |
| 2,982,793 | A | 5/1961 | Turner et al. |
| 2,987,487 | A | 6/1961 | Stevens et al. |
| 3,025,248 | A | 3/1962 | Rosinski |
| 3,068,303 | A | 12/1962 | Pattison |
| 3,108,888 | A | 10/1963 | Bugosh |
| 3,141,742 | A | 7/1964 | Dye et al. |
| 3,235,515 | A | 2/1966 | Earl |
| 3,270,059 | A | 8/1966 | Siegfried Winderl et al. |
| 3,331,787 | A | 7/1967 | Keith et al. |
| 3,344,196 | A | 9/1967 | Hubert et al. |
| 3,397,154 | A | 8/1968 | Herbert |
| 3,403,111 | A | 9/1968 | Colgan et al. |
| 3,407,149 | A | 10/1968 | Taylor et al. |
| 3,423,194 | A | 1/1969 | Kearby |
| 3,437,586 | A | 4/1969 | Weisz |
| 3,441,251 | A | 4/1969 | Burns |
| 3,565,830 | A | 2/1971 | Keith et al. |
| 3,591,649 | A | 7/1971 | Kroll et al. |

(Continued)

FOREIGN PATENT DOCUMENTS

| EP | 0 042 471 A1 | 12/1981 |
| EP | 0042471 | 12/1981 |
| EP | 0296726 | 12/1988 |
| EP | 313375 | 4/1989 |
| EP | 690119 | 1/1996 |
| EP | 0736326 | 10/1996 |
| EP | 1129776 | 9/2001 |
| EP | 1445018 | 8/2004 |
| EP | 1632289 | 3/2006 |
| GB | 1183201 | 3/1970 |

(Continued)

OTHER PUBLICATIONS de Kerk, A. et al. (2010). Catalysis in the Refining of Fischer-Tropsch Syncrude, Royal Society of Chemistry, 294 pgs (Office action cites pp. 11 and 15).*

(Continued)

Primary Examiner — Brian McCaig
(74) Attorney, Agent, or Firm — Patterson Thuente Pedersen, P.A.

(57) ABSTRACT

A method of producing an aluminum oxide supported catalyst for use in a Fischer-Tropsch synthesis reaction, which comprises: spray-drying a slurry of γ-alumina and a source of a spinel forming metal to form a solid precursor material; calcining the precursor material to form a modified support material including a metal aluminate spinel; impregnating the modified alumina support material with a source of cobalt; calcining the impregnated support material, and activating the catalyst.

61 Claims, No Drawings

(56) References Cited

U.S. PATENT DOCUMENTS

| | | | |
|---|---|---|---|
| 3,692,701 A | 9/1972 | Box et al. |
| 3,751,508 A | 8/1973 | Fujiso et al. |
| 3,825,504 A | 7/1974 | Hilfman |
| 3,840,471 A | 10/1974 | Acres |
| 3,853,790 A | 12/1974 | Vosolsobe et al. |
| 3,876,557 A | 4/1975 | Bland |
| 3,881,696 A | 5/1975 | Lepeytre et al. |
| 3,883,444 A | 5/1975 | Maselli et al. |
| 3,933,883 A | 1/1976 | Parthasarathy et al. |
| 3,966,640 A | 6/1976 | Katz et al. |
| 3,988,263 A | 10/1976 | Hansford |
| 4,049,582 A | 9/1977 | Erickson et al. |
| 4,055,513 A | 10/1977 | Wheelock |
| 4,065,484 A | 12/1977 | Dobashi |
| 4,080,390 A | 3/1978 | Imamura |
| 4,088,608 A | 5/1978 | Tanaka et al. |
| 4,102,777 A | 7/1978 | Wheelock |
| 4,102,822 A | 7/1978 | Mulaskey |
| 4,191,664 A | 3/1980 | McArthur |
| 4,200,552 A | 4/1980 | Noguchi et al. |
| 4,219,444 A | 8/1980 | Hill et al. |
| 4,233,186 A | 11/1980 | Duprez et al. |
| 4,237,030 A | 12/1980 | Noguchi et al. |
| 4,247,730 A | 1/1981 | Brunelle |
| 4,285,837 A | 8/1981 | Sato et al. |
| 4,368,142 A | 1/1983 | Frohning et al. |
| 4,440,956 A | 4/1984 | Couvillion |
| 4,454,207 A | 6/1984 | Fraioli et al. |
| 4,456,703 A | 6/1984 | Aldridge |
| 4,499,209 A | 2/1985 | Hoek et al. |
| 4,539,310 A | 9/1985 | Leftin et al. |
| 4,585,798 A | 4/1986 | Beuther et al. |
| 4,595,703 A | 6/1986 | Payne et al. |
| 4,610,975 A | 9/1986 | Baker et al. |
| 4,613,624 A | 9/1986 | Beuther et al. |
| 4,626,521 A | 12/1986 | Murib |
| 4,670,414 A | 6/1987 | Kobylinski et al. |
| 4,717,702 A | 1/1988 | Beuther et al. |
| 4,729,981 A | 3/1988 | Kobylinski et al. |
| 4,801,573 A | 1/1989 | Eri et al. |
| 4,801,620 A | 1/1989 | Fujitani et al. |
| 4,844,837 A | 7/1989 | Heck et al. |
| 4,857,559 A | 8/1989 | Eri et al. |
| 4,870,044 A | 9/1989 | Kukes et al. |
| 4,880,763 A | 11/1989 | Eri et al. |
| 4,888,316 A | 12/1989 | Gardner et al. |
| 4,895,816 A | 1/1990 | Gardner et al. |
| 4,957,896 A | 9/1990 | Matsumoto et al. |
| 4,968,660 A | 11/1990 | Tijburg et al. |
| 4,977,126 A | 12/1990 | Mauldin et al. |
| 4,985,387 A | 1/1991 | Prigent et al. |
| 4,988,661 A | 1/1991 | Arai |
| 5,037,792 A | 8/1991 | Luck |
| 5,100,859 A | 3/1992 | Gerdes et al. |
| 5,102,851 A | 4/1992 | Eri et al. |
| 5,110,780 A | 5/1992 | Peters |
| 5,116,801 A | 5/1992 | Luck |
| 5,116,879 A | 5/1992 | Eri et al. |
| 5,268,091 A | 12/1993 | Boitiaux et al. |
| 5,380,697 A | 1/1995 | Matusz et al. |
| 5,552,363 A | 9/1996 | Pannell et al. |
| 5,565,092 A | 10/1996 | Pannell et al. |
| 5,565,400 A | 10/1996 | Holmgren |
| 5,639,798 A | 6/1997 | Wilson et al. |
| 5,744,419 A | 4/1998 | Choudhary et al. |
| 5,851,948 A | 12/1998 | Chuang et al. |
| 5,856,263 A | 1/1999 | Bhasin et al. |
| 5,874,381 A | 2/1999 | Bonne et al. |
| 5,965,481 A | 10/1999 | Durand et al. |
| 5,977,012 A | 11/1999 | Kharas et al. |
| 6,019,954 A | 2/2000 | Tang et al. |
| 6,022,755 A | 2/2000 | Kinnari et al. |
| 6,069,111 A | 5/2000 | Yamamoto et al. |
| 6,075,062 A | 6/2000 | Zennaro et al. |
| 6,100,304 A | 8/2000 | Singleton et al. |
| 6,211,255 B1 | 4/2001 | Schanke et al. |
| 6,235,798 B1 | 5/2001 | Roy et al. |
| 6,255,358 B1 | 7/2001 | Singleton et al. |
| 6,262,132 B1 | 7/2001 | Singleton et al. |
| 6,271,432 B2 | 8/2001 | Singleton et al. |
| 6,284,217 B1 | 9/2001 | Wang et al. |
| 6,365,544 B2 | 4/2002 | Herron et al. |
| 6,465,530 B2 | 10/2002 | Roy-Auberger et al. |
| 6,472,441 B1 | 10/2002 | Kibby |
| 6,486,220 B1 | 11/2002 | Wright |
| 6,486,221 B2 | 11/2002 | Lapidus et al. |
| 6,515,035 B2 | 2/2003 | Roy-Auberger et al. |
| 6,537,945 B2 | 3/2003 | Singleton et al. |
| 6,596,667 B2 | 7/2003 | Bellussi et al. |
| 6,596,781 B1 | 7/2003 | Schinski |
| 6,649,803 B2 | 11/2003 | Mart et al. |
| 6,689,819 B2 | 2/2004 | Bellussi et al. |
| 6,696,502 B1 | 2/2004 | Mart et al. |
| 6,734,137 B2 | 5/2004 | Wang et al. |
| 6,780,817 B1 | 8/2004 | Koyama |
| 6,800,664 B1 | 10/2004 | Espinoza et al. |
| 6,818,589 B1 | 11/2004 | Gillespie |
| 6,822,008 B2 | 11/2004 | Srinivasan et al. |
| 6,825,237 B2 | 11/2004 | Schweitzer et al. |
| 6,835,690 B2 | 12/2004 | Van Berge et al. |
| 6,835,756 B2 | 12/2004 | Font Freide et al. |
| 6,927,190 B2 | 8/2005 | Lok et al. |
| 6,958,310 B2 | 10/2005 | Wang et al. |
| 7,011,809 B2 | 3/2006 | Singleton et al. |
| 7,012,103 B2 | 3/2006 | Espinoza et al. |
| 7,012,104 B2 | 3/2006 | Espinoza et al. |
| RE39,073 E | 4/2006 | Herbolzheimer et al. |
| 7,022,644 B2 | 4/2006 | Foong et al. |
| 7,041,866 B1 | 5/2006 | Gillespie |
| 7,045,554 B2 | 5/2006 | Raje et al. |
| 7,067,562 B2 | 6/2006 | Espinoza et al. |
| 7,071,239 B2 | 7/2006 | Ortego et al. |
| 7,078,439 B2 | 7/2006 | Odueyungbo et al. |
| 7,097,786 B2 | 8/2006 | Dindi et al. |
| 7,163,963 B2 | 1/2007 | Fraenkel |
| 7,226,574 B2 | 6/2007 | Long et al. |
| 7,230,035 B2 | 6/2007 | Espinoza et al. |
| 7,253,136 B2 | 8/2007 | Mauldin et al. |
| 7,256,154 B2 | 8/2007 | Moon et al. |
| 7,276,540 B2 | 10/2007 | Espinoza et al. |
| 7,341,976 B2 | 3/2008 | Espinoza et al. |
| 7,351,393 B1 | 4/2008 | Bayense et al. |
| 7,351,679 B2 | 4/2008 | Eri et al. |
| 7,361,626 B2 | 4/2008 | Baijense et al. |
| 7,365,040 B2 | 4/2008 | Van Berge et al. |
| 7,402,612 B2 | 7/2008 | Jin et al. |
| 7,417,073 B2 | 8/2008 | Mauldin et al. |
| 7,422,995 B2 | 9/2008 | Baijense et al. |
| 7,452,844 B2 | 11/2008 | Hu et al. |
| 7,473,667 B2 | 1/2009 | Hagemeyer et al. |
| 7,541,310 B2 | 6/2009 | Espinoza et al. |
| 7,560,412 B2 * | 7/2009 | Osbourne et al. ............ 502/327 |
| 8,143,186 B2 | 3/2012 | Rytter |
| 8,324,128 B2 | 12/2012 | Rytter et al. |
| 2001/0031793 A1 | 10/2001 | Singleton et al. |
| 2001/0032965 A1 | 10/2001 | Wang et al. |
| 2001/0051588 A1 | 12/2001 | Herron et al. |
| 2002/0028853 A1 | 3/2002 | Manzer et al. |
| 2002/0094932 A1 | 7/2002 | Faber et al. |
| 2002/0131914 A1 | 9/2002 | Sung |
| 2002/0172642 A1 | 11/2002 | Dindi et al. |
| 2003/0119668 A1 | 6/2003 | Lok et al. |
| 2003/0158037 A1 | 8/2003 | Foong et al. |
| 2003/0203982 A1 * | 10/2003 | Davis et al. .................. 518/719 |
| 2004/0054016 A1 | 3/2004 | Lu et al. |
| 2004/0077737 A1 | 4/2004 | Eri et al. |
| 2004/0110852 A1 | 6/2004 | Srinivasan et al. |
| 2004/0127585 A1 | 7/2004 | Raje |
| 2004/0132834 A1 | 7/2004 | Ortego et al. |
| 2004/0138060 A1 | 7/2004 | Rapier et al. |
| 2004/0138317 A1 | 7/2004 | Xie et al. |
| 2004/0180784 A1 | 9/2004 | Hagemeyer et al. |
| 2004/0204506 A1 | 10/2004 | Mauldin et al. |
| 2005/0184009 A1 | 8/2005 | Jansen et al. |

(56) References Cited

U.S. PATENT DOCUMENTS

| | | |
|---|---|---|
| 2005/0245621 A1 | 11/2005 | Baijense et al. |
| 2005/0272827 A1 | 12/2005 | Lok |
| 2006/0009352 A1 | 1/2006 | Zhao et al. |
| 2006/0167119 A1 | 7/2006 | Leng et al. |
| 2006/0223693 A1 | 10/2006 | Fujimoto et al. |
| 2007/0099797 A1 | 5/2007 | Hu et al. |
| 2007/0161714 A1 | 7/2007 | Rytter et al. |
| 2008/0064770 A1 | 3/2008 | Rytter et al. |
| 2008/0255256 A1 | 10/2008 | Rytter |
| 2010/0022388 A1 | 1/2010 | Soled et al. |
| 2010/0022670 A1 | 1/2010 | Soled et al. |
| 2010/0029792 A1 | 2/2010 | Diehl et al. |
| 2010/0099780 A1 | 4/2010 | Rytter et al. |
| 2010/0184872 A1 | 7/2010 | Eri et al. |

FOREIGN PATENT DOCUMENTS

| | | |
|---|---|---|
| GB | 2053712 | 2/1981 |
| GB | 2258826 | 2/1993 |
| GB | 2416715 | 2/2006 |
| JP | 58139744 | 8/1983 |
| JP | 2003024786 | 1/2003 |
| WO | WO9312879 | 7/1993 |
| WO | WO96/00613 | 1/1996 |
| WO | WO99/42214 | 8/1999 |
| WO | WO99/61143 | 12/1999 |
| WO | WO00/20116 | 4/2000 |
| WO | WO00/25918 | 5/2000 |
| WO | WO01/36352 | 5/2001 |
| WO | WO01/62381 | 8/2001 |
| WO | WO02/02229 | 1/2002 |
| WO | WO02/47816 | 6/2002 |
| WO | WO02/089978 | 11/2002 |
| WO | WO03/002252 | 1/2003 |
| WO | WO2004/035193 | 4/2004 |
| WO | WO2005/060448 | 7/2005 |
| WO | WO2005/072866 | 8/2005 |
| WO | WO 2005/072866 A1 | 8/2005 |
| WO | WO2006/010936 | 2/2006 |
| WO | WO2006/067285 | 6/2006 |
| WO | WO 2006/115668 A1 | 11/2006 |
| WO | WO2007/093825 | 8/2007 |
| WO | WO 2008/129034 A1 | 10/2008 |
| WO | WO2009/118372 | 10/2009 |
| WO | WO 2011/027104 A1 | 3/2011 |

OTHER PUBLICATIONS

Chorkendorff, I. et al. (2007). Concepts of Modern Catalysis and Kinetics, 2$^{nd}$ ed, Wiley-VCH Verlag GmbH & Co, 457 pgs (Office action cites p. 194).*
Gates, B.C. et al. (1979). Chemistry of Catalytic Processes, 464 pgs (Office action cites p. 250).*
Satterfield, C.N. (1980). Heterogenous Catalysis in Practice, Mcgraw-Hill, 416 pgs (Office action cites p. 79).*
Dancuart, L.P. et al. (2007). Studies in Surface Science and Catalysis, 163, 379-399.*
Compressed Air and Gas Institute (What is Clean, Dry Air?) Tap #106, published Nov. 1, 2005.
Stevens et al., Qatar Fertilizer Company, in the proceedings of Nitrogen + Syngas 2008 conference conducted in Moscow, pp. 20-23. Apr. 2008.
Catalyst Handbook, 2nd edition, M.V. Twigg, editor Wolfe Publishing, London 1989. pp. 77-81.
Luo et al., "Fischer-Tropsch Synthesis: Group II alkali-earth metal promoted catalysts", Applied Catalysis. pp. 171-181 (2003).
Madikizela et al. Applied Catalysis A: General 272 (2004) 339-346.
International Search Report for International Application No. PCT/GB2008/000300 dated Jul. 25, 2008.
Betancourt, P et al., "A Study of the Ruthenium-Alumina System", Applied Catalysis A: General. vol. 170, pp. 307-314 (1998).
Van De Loosdrecht et al., "Calcination of Co-based Fischer-Tropsch Synthesis Catalysts," Topics of Catalysis, vol. 26, Nos. 1-4, pp. 121-127. (Dec. 2003).
Borg, Øyvind et al., "Effect of Calcination Atmosphere and Temperature on γ-Al$_2$O$_3$ Supported Colbalt Fischer-Tropsch Catalysts,"Topics in Catalysis, vol. 45, Nos. 1-4, pp. 39-43 (Aug. 2007).
Schulz, "Major and Minor Reactions in Fischer-Tropsch Synthesis on Colbalt Catalysts" Topics in Catalysis, 26 91-4): 73-85 (2003).
Li Fan et al., Supercritical-phase Process for Selective Synthesis of Wax from Syngas: Catalyst and Process Development. Catalysis Today, 36:295-306/ 1997.
ASTM Standard D4058-96, 2001, "Standard Test Method for Attrition and Abrasion of Catalysts and Catalyst Carriers", ASTM Int'l. West Conshohoken, PA. Viewed on Feb. 19, 2009 at http://www.astm.org/DATABASE.CART/HISTORICAL/D4058-96R01.htm.
International Search Report for International Application No. PCT/GB2005/003675 dated Dec. 9, 2005 and GB0421242.9. dated Aug. 17, 2005.
International Search Report for International Application No. PCT/GB2005/000287 dated May 18, 2005 and GB0401829.7 dated May 6, 2005.
Iglesia et al., "Selectivity Control and Catalyst Design in the Fischer-Tropsch Synthesis: Site, Pellets and Reactors", Advances in Catalysis, vol. 3. (1993).
Saib et al., "Silica supported colbalt Fischer-Tropsch catalysts: Effect of Pore Diameter of Support", Catalysis Today, 71: 395-402 (2002).
Tang et al., "Partial Oxidation of Methane of Synthesis Gas Over Alpha-AL203-Supported Bimetallic PT-CO Catalysts", Catalysis Letters, Baltzer, Scientific Publ, Basel, Ch. vol. 59, No. 2/4. Jun. 1999. pp. 129-135.
Oukaci et al., "Comparison of patented Co. F-T catalysts using fixed-bed and slurry bubble column reactors" Applied Catalysis A: General Elsevier Scienc, Amsterdamn, NL, vol. 186, No. 1-2. Oct. 4, 1999, pp. 120-144.
Iglesia et al., "Reactions-Transport Selectivity Models and the Design of Fischer-Tropsch Catalysts,"Computer-Aided Design of Catalysts, Edited by Becker and Pereira. Ch. 7. pp. 199-257. 1993.
Jacobs et al, "Fischer-Tropsch Synthesis XAFS XAFS studies of the effect of water on a PT-promoted Ca/Al$_2$O$_3$ catalyst", Applied Catalysis, 247:335-343. (2003).
International Search Report for International Application No. PCT/GB2010/002111 dated May 25, 2012.
International Search Report for International Application No. PCT/GB01/05461 dated Mar. 1, 2002.
International Search Report for International Application No. PCT/GB03/04873 dated Mar. 25, 2004.
International Search Report for International Application No. PCT/GB2010/001647 dated Nov. 2, 2010.
Application and File History for U.S. Appl. No. 10/433,846, filed Nov. 10, 2003, inventors Eri et al.
Taylor, "An Introduction to Error Analysis", 2nd Ed. (1997). 329 pages. Chs. 1 and 2 provided.
Application and File History for U.S. Appl. No. 10/535,066, filed Mar. 15, 2006, inventors Rytter et al.
Application and File History for U.S. Appl. No. 10/587,825, filed Feb. 2, 2007 inventors Rytter et al.
Application and File History for U.S. Appl. No. 11/663,663, filed Feb. 14, 2008, inventor Rytter.
Application and File History for U.S. Appl. No. 12/525,070, filed Mar. 26, 2010, inventors Ed et al.
Application and File History for U.S. Appl. No. 12/582,541, filed Oct. 20, 2009, inventor Rytter et al.
Application and File History for U.S. Appl. No. 13/378,581, filed Dec. 15, 2011, inventors Rytter et al.
Application and File History for U.S. Appl. No. 13/510,867, filed Sep. 24, 2012, inventors Rytter et al.
Khassin et al., Cobalt-aluminum co-precipitated catalysts and their performance in the Fischer-Tropsch synthesis, Journal of Molecular Catalysis A: Chemical 168 (2001) 193-207.

* cited by examiner

FISCHER-TROPSCH CATALYSTS

The present application is a National Phase entry of PCT Application No. PCT/GB2011/001149 filed Jul. 29, 2011, which claims priority from U.S. Application No. 61/371,912, filed Aug. 9, 2010, the disclosures of which are hereby incorporated by reference in their entireties.

FIELD OF THE INVENTION

The present invention relates to supported catalysts and their use in Fischer-Tropsch synthesis reactions, and more specifically to a process for the production of the catalyst, and to the catalyst itself.

BACKGROUND OF THE INVENTION

Conversion of natural gas to liquid hydrocarbons ("Gas To Liquids" or "GTL" process) is based on a 3 step procedure consisting of: 1) synthesis gas production; 2) synthesis gas conversion by Fischer-Tropsch ("FT") synthesis; and 3) upgrading of FT products (wax and naphtha/distillates) to final products.

The Fischer-Tropsch reaction for conversion of synthesis gas, a mixture of CO and hydrogen, possibly also containing essentially inert components like $CO_2$, nitrogen and methane, is commercially operated over catalysts containing the active metals Fe or Co. Iron catalysts are best suited for synthesis gas with low $H_2$/CO ratios (<1.2), e.g. synthesis gas produced from coal or other heavy hydrocarbon feedstock, where this ratio is considerably lower than the consumption ratio of the FT-reaction (2.0-2.1).

To achieve sufficient catalytic activity, it is customary to disperse a catalytically active metal on a catalyst carrier, often referred to as the support material. In this way, a larger portion of the metal is exposed as surface atoms where the reaction can take place. Typically, support materials are alumina, silica and titania based. In addition, different promoters are also added to further increase catalytic activity, and typical promoters may be rhenium, ruthenium and platinum. The F-T process can be carried out either in a fixed bed reactor or a slurry bed reactor. In case of a slurry bed process, the catalyst particles are suspended in oil with gaseous reactants being bubbled into the reactor. For either process to be economically viable, the catalyst must exhibit good performance for a long period of time without significant loss in catalytic activity. Typically, catalyst deactivates because of one or more of the following issues: (a) poisoning of the active catalytic metal (e.g. cobalt), (b) loss of catalytic metal surface area (e.g. via sintering), (c) loss of active metal species due to reaction with support, and (d) attrition.

The attrition of the catalyst, i.e. issue (d) above, is primarily dependent on the strength of the support for the catalytically active metal. Using slurry bed catalysts are subjected to a number of collisions either with other particles or with the reactor walls. This causes the catalyst particles to "attrit" or break into smaller particles. Smaller particles are not retained in the reactor, and as a result the activity declines absent continuous addition of fresh catalyst. In order to enhance performance of the catalyst and to improve the catalyst life, a support must therefore exhibit high attrition resistance.

High surface area alumina is commonly used as a catalyst support for F-T. Supports having high surface area provide the necessary support for dispersing catalytic sites throughout the catalyst. High surface area aluminas are conventionally prepared by calcining an aluminum hydroxide composition such as boehmite. Calcined, high surface area alumina per se, however, does not exhibit good attrition resistance. Indeed, it is also largely believed that aluminas after calcination cannot be easily bound into hard particles. Hence, there is a tendency to use boehmite aluminas as support precursors, which are slurried in water and "peptized" in the presence of an acid such as nitric or hydrochloric acid, followed by drying and calcinations to give attrition resistant particles. This alternative presents its own problem because these peptized boehmitic aluminas slurries gel at high solids content and need to be diluted before drying and calcination. Processing the alumina at high solids content is desirable not only to get high production rates, but also to yield a strong particle of desired particle size upon spray drying.

In addition, and as reference with respect to issue (c) above, high surface area alumina supports react with active metal precursor of cobalt to form Co-aluminate spinel upon calcination. This transforms the active Co metal to "inactive" spinel Co-aluminate and thus decreases the catalyst activity.

In order to prevent Co-aluminate spinel formulation, divalent metals like Ni, Zn, and Mg can be added to an alumina support to form the spinel phase "a priori" and thus prevent the formation of inactive Co-aluminate. The divalent metal aluminate spinels are formed upon high temperature calcinations above 650° C. Such spinel materials do not exhibit high strength, however, and can easily break into smaller particles. In other words, such spinel phase-based particles generally do not have sufficient attrition resistance.

It has been shown that if the spinels compositions are calcined at very high temperatures, in excess of 1100° C., the attrition resistance improves significantly (see WO 2005/072866 A1 or US 2007/0161714). In addition to requiring high calcination temperatures, it is also apparent that high levels of divalent metals are needed to attain the good attrition resistance. Typically, the divalent compound is in excess of 10 wt % (as metal) in loading.

It has also been shown that, as a result of high temperature calcinations, the support pore diameter shifts to high pore modes. Catalysts made from these high temperature calcined spinel supports therefore have high selectivity to high hydrocarbons in addition to the aforementioned attrition resistance. The practical use of these supports, however, is limited due to expensive processing steps, and large amounts of expensive divalent metal compounds added as dopants. Furthermore, large amount of divalent dopant compounds poses the risk of leaching out of the spinel structure and adversely affecting the catalyst activity.

SUMMARY OF THE INVENTION

It is an object of the present invention to provide a method of producing such a catalyst with a high resistance to attrition and at a lower cost, minimizing the amount of costly components and costly processing steps.

Certain aspects of the present invention are concerned with aluminium oxide, as a support material.

According to one aspect of the invention, there is provided a method of producing a modified aluminium oxide supported catalyst, which comprises the following steps: an initial step of forming a slurry by mixing aluminium oxide and a metal compound capable of forming a spinel phase and a soluble compound of trivalent aluminium; a shaping step in which solid material from the slurry is shaped into a solid precursor material; a first calcination step in which the precursor material is calcined at a temperature of at least 700° C. to produce a modified aluminium oxide support material including a metal aluminate spinel phase compound formed by the metal capable of forming a spinel phase and the aluminium oxide; an impregnation step in which the modified aluminium oxide support material is impregnated with a source of catalytically active metal; and a second calcination step in which the impregnated modified aluminium oxide support material is calcined at a temperature of at least 150° C. to produce the modified aluminium oxide supported catalyst.

Preferably, the aluminium oxide is selected from the group consisting of gamma alumina, delta alumina, theta alumina, eta alumina, rho alumina and mixtures thereof. Preferably, the aluminium oxide predominantly comprises gamma alumina. Preferably, the gamma alumina is prepared by heating boehmite alumina at a temperature sufficient to convert boehmite alumina to gamma alumina. Preferably, the boehmite alumina is heated to a temperature in the range of 400° C. to 700° C.

The metal capable of forming a spinel phase with aluminium oxide will hereinafter be referred to as "the spinel forming metal" and is a divalent.

Preferably, the source of the spinel forming metal comprises a source of cobalt, zinc, copper, magnesium, calcium, manganese, nickel or iron. Preferably, the source of the spinel forming metal is a soluble metal salt and is preferably selected from the group consisting of zinc nitrate, nickel nitrate, and magnesium nitrate. Preferably the amount of spinel forming metal added is in the range of 1 to 50 wt %, expressed as the wt % of the spinel forming metal based on the total weight of modified support preferably 2 to 20 wt %, more preferably 3 to 12 wt %.

A soluble compound of trivalent aluminium is combined in the slurry of alumina and the spinel forming metal. Preferably, the soluble compound of trivalent aluminium is selected from the group consisting of aluminium nitrate, aluminium chlorohydrol, aluminium sulphate, aluminium chloride, aluminium acetate, aluminium formate.

Preferably, mixing the slurry reduces the particle size of solids in the mixture to a median particle size that is less then than ten microns, preferably without significant gelling. The mixing may be conducted in a mill. Preferably, the mixing reduces the particle size of solids in the mixture to a median particle size in the range of 1 to 5 μm.

Preferably, the first calcination step is carried out at a temperature in the range of 700 to 1300° C., more preferably at a temperature in the range of 700 to 1050° C., preferably 900 to 1050° C. Optionally, the product from the first calcination step, further comprises alpha alumina.

Optionally, before the shaping step, the solid material is washed at least once. Preferably the washing is performed with water containing less than 300 ppm calcium and/or less than 300 ppm sodium. Preferably, the material from the slurry is dried at a temperature in the range of 100 to 400° C. to form particles having a median particle size in the range of 20 to 100 microns, prior to the first calcination. Preferably, the drying is carried out in a spray drier. Preferably, the forming step is selected from the group consisting of spray-drying, peletization and extrusion.

The first calcination step may be carried out in several calcination steps, each of which covers a part of the temperature range up to the maximum temperature.

A preferred embodiment is constituted by a method in which the modified aluminium oxide support is produced by: combining aluminium oxide selected from the group consisting of gamma alumina, delta alumina, theta alumina, eta alumina and mixtures thereof, a 2-valent and/or soluble compound of a spinel forming metal, or mixture of metals, and a soluble compound of trivalent aluminium selected from the group consisting of aluminium nitrate, aluminium chlorohydrol, aluminium sulphate, aluminium chloride and mixtures thereof; reducing the particle size of the solids in the mixture to a median particle size of less than ten microns; drying the mixture at a temperature in the range of 100 to 400° C.; and calcining the dried mixture at a temperature in the range of 700 to 1300° C.

Preferably, in this method, the particle size of solids in the mixture is reduced to a median particle size in the range of 1 to 5 microns, the mixture is dried at a temperature in the range of 100 to 400° C., and the dried mixture is calcined at a temperature in the range of 700 to 1050° C. Preferably, the aluminium oxide is gamma alumina, the spinel forming metal compound is a metal nitrate salt and the trivalent aluminium is aluminium nitrate. Preferably, the method includes drying the mixture at a temperature in the range of 100 to 400° C. to form particles having a median particle size in the range of 20 to 100 microns prior to the first calcination step.

Another important step in the catalyst preparation is the impregnation with catalytically active metal. A number of different procedures have been described in the literature, including the case of alternative solvents and chemicals. Preferably, in the present invention, the impregnation step comprises an incipient wetness treatment in which an aqueous solution of the catalytically active metal is mixed with the modified support material until the pores are filled and the impregnated modified support material is then dried, prior to the second calcination step.

The preferred procedure involves aqueous incipient wetness with solutions of cobalt nitrate ($Co(NO_3)_2$) and perrhenic acid ($HReO_4$). Alternatives include using cobalt acetate(s), cobalt halide(s), cobalt carbonyl(s), cobalt oxalate(s), cobalt phosphate(s), cobalt (hexa)amine salt(s), organic cobalt compounds, ammonium perrhenate, rhenium halide(s), rhenium carbonyl(s), industrial metal salt solutions and organic solvents. However, the impregnation technique may encompass all available methods besides incipient wetness, such as precipitation, impregnation from slurry with surplus liquid, chemical vapor deposition, etc.

Impregnation may be in a single or multiple steps from a mixed aqueous solution of appropriate metal salts, generally of cobalt nitrate and perrhenic acid. Preferably, the impregnation technique is by the pore filling or "incipient wetness" method that implies that the solution is mixed with the dry support until the pores are filled. The definition of the end point of this method may vary somewhat from laboratory to laboratory, giving an impregnated catalyst that has a completely dry appearance to one which appears sticky or snow-like. However, in no instance is there any free flowing liquid present. Preferably, the amount of aqueous solution used in the impregnation is 0.05-2 times larger than the measured pore volume of the catalyst support.

The impregnated catalyst is dried, preferably at 80-120° C., to remove water from the catalyst pores before being calcined at preferably 200-600° C.

There are several variations to these procedures that will not affect the essence of the invention. The calcinations in the present case are preferably performed in a stationary oven with a certain temperature ramping speed of 2° C./min. It should be understood that the ramping speed could be varied and that any standard or specially designed calcination equipment could be applied by adjusting the conditions properly. Examples of such calcination equipment are continuous or batch-wise operated rotational calciners and conveyor belt type calciners.

Preferably, after impregnation the cobalt content of the impregnated modified support material is in the range of 3 to 60 wt %, measured as the metal weight of the total catalyst after reduction, preferably 5 to 30 wt %, more preferably 8 to 18 wt %. Preferably, the impregnated modified support material is calcined at a temperature in the range 200 to 600° C. Preferably after the second calcination step, the supported catalyst material is activated. Preferably, the activation step comprises reduction of a substantial portion of the catalytically active metal compound present to the metal, preferably more than 60%, more preferably more than 70%. Preferably, the reduction is carried out by treating the catalyst material with a reducing gas. Preferably, the reducing gas is selected from the group consisting of hydrogen, carbon monoxide and a mixture thereof, optionally mixed with an inert gas. Preferably, the reduction is carried out at an activation temperature in the range 20 to 500° C., more preferably in the range 250 to 400° C.

Preferably, prior to impregnation, the modified support has an ASTM attrition modified value of less than 10%, preferably less than 5%, more preferably less than 2%.

The present invention extends to a catalyst produced by a method according to the present invention, which comprises a support derived from aluminium oxide in the presence of a soluble compound of trivalent aluminium, the aluminium oxide being modified by the presence of a spinel phase formed from the aluminium oxide and spinel forming metal, and impregnated with a catalytically active metal, whereby the spinel is substantially homogeneously distributed throughout the aluminium oxide and the catalytically active metal is absorbed on to the surface of the modified support particles.

Preferably, the source of spinel forming metal is soluble compound. The spinel forming metal preferably comprises nickel or zinc and the catalytically active metal is preferably cobalt. Preferably, the cobalt content of the catalyst is from 5 to 30% by weight, preferably 8 to 18% by weight. The catalyst may include a promoter, preferably up to 3% by weight. Preferably, the promoter is selected from rhenium and platinum.

The present invention also extends to a process for the production of hydrocarbons which comprises subjecting $H_2$ and CO gases to a Fischer-Tropsch synthesis reaction in a reactor in the presence of the catalyst of the present invention.

Preferably, the Fischer-Tropsch synthesis reaction is a three-phase reaction in which the reactants are gaseous, the product is at least partially liquid and the catalyst is solid. Preferably, the reaction is carried out in a slurry bubble column reactor. Preferably, the $H_2$ and CO are supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry.

Preferably the reaction temperature is in the range 190 to 280° C., preferably 210 to 250° C., and the pressure is in the range 10 to 60 bar, preferably 15 to 35 bar. Preferably the ratio $H_2$/CO of the gases supplied to the Fischer-Tropsch synthesis reactor is in the range 1.1 to 2.2, preferably 1.5 to 1.95, and the superficial gas velocity in the reactor is in the range 5 to 60 cm/s, preferably 20 to 40 cm/s.

Preferably, the product of the Fischer-Tropsch synthesis reaction is subsequently subjected to post-processing. The post-processing may include de-waxing hydro-isomerization, hydro-cracking and combinations of these.

The present invention is generally but not exclusively concerned with Co-based catalysts, in particular, supported Co-based catalysts. A variety of products can be made by the FT-reaction, but from supported cobalt, the primary product is long-chain hydrocarbons that can be further upgraded to products like diesel fuel and petrochemical naphtha. Byproducts can include olefins and oxygenates.

The present invention may be carried into practice in various ways and will now be illustrated in the following non-limiting examples.

DETAILED DESCRIPTION OF THE INVENTION

Metal Aluminate Spinel

The term "metal aluminate spinel" in the context of the present invention refers to the conventional definition of a spinel phase, i.e., a crystal structure possessing double oxides having a formula of $AB_2O_4$, wherein A and B each represent a metal element. The spinel in the present invention is an aluminate spinel, and therefore metal B is trivalent Al. Metal A is a divalent metal that varies and depends on the spinel forming metal source. Spinel structures are crystalline, and possess a closely packed, oxygen containing cubic lattice with the A and B metals in interstitial tetrahedral and octahedral holes. The term spinel includes normal spinels, inverse spinels and disordered spinel. The metal aluminate spinel is believed to result from the aluminium oxide and spinel forming metal compound capable of forming a spinel phase.

Aluminium Oxide and Alumina

The terms aluminium oxide and alumina are used herein to include not only those compositions of $Al_2O_3$, but also aluminium and oxygen-containing hydrous compositions such as aluminium hydroxide, and aluminium oxyhydroxide. The aluminium oxide is believed to be a precursor for the aluminate of the metal spinel when calcined in the presence of a spinel forming metal. The aluminium oxide is insoluble and added as a powder, or other solid form suitable for forming aluminate when calcined in the presence of the spinel forming metal source.

Suitable examples of aluminium oxide include, without being limited to, transitional aluminas, and crystalline hydrous alumina, such as crystalline aluminium hydroxide. Suitable transition aluminas include gamma-alumina; eta-alumina; delta-alumina; theta-alumina, rho-alumina and any combinations of two or more thereof. These aluminas are known as anhydrous aluminas. Suitable crystalline aluminium hydroxides include precursors to metastable forms of transition aluminas, such as gibbsite, bayerite, nordstrandite, and tohdite. Gibbsite ($Al(OH)_3$), bayerite (a polymorph of gibbsite), and nordstrandite are crystalline forms of aluminium trihydroxide. Suitable aluminium oxyhdroxides include diaspore and boehmite (AlOOH).

Gamma alumina is a particularly suitable aluminium oxide for use in various embodiments of the present invention. Gamma alumina can be prepared by converting boehmite alumina to gamma alumina by calcining boehmite to a temperature of at least 350° C., and more typically in the range of 400 to 700° C. Desired calcinations can be achieved in a stationary muffle furnace or a rotary furnace. In the case of a muffle furnace, the boehmite alumina is heated at a temperature in the above range for a period of from about 15 minutes to about 24 hours (more preferably from about 30 minutes to about 8 hours and most preferably about 2 hours). Examples of commercially-supplied boehmite materials suitable for forming gamma alumina supports include CATAPAL and PURAL aluminas supplied by Sasol (formerly Condea/Vista). Details can be found in U.S. Pat. No. 7,011,809, the teaching of which is incorporated by reference herein.

It is particularly advantageous in later processing to utilize gamma alumina, or to convert boehmite to gamma alumina to be the aluminium oxide. Using gamma alumina enables the solids in subsequent processing steps, e.g., in a dryer, to be relatively high (>20 wt %). Processing the aluminium oxide composition at high solids is desirable not only to attain high production rates, but also to yield a strong particle of a desired particle size upon spray drying. Typically about 25-30% solids can be used in this process when aluminium oxide is gamma alumina. The aluminium oxide is typically in powder form having an average particle size in the range of 10 to 100 microns. The surface area and pore volume of the aluminium oxide can vary, and these parameters will dictate the surface area and porosity of the final support. By way of example, the aluminium oxide can have a surface area in the range of 100 to 400 m$^2$/g and pore volume in the range of 0.2 to 1.2 cc/g.

The aluminium oxide may be optionally washed, especially if the aluminium oxide is prepared from sources containing impurities, such as sulfur, alkali metal and other metallic species such as calcium. The aluminium oxide can be washed in deionized aqueous baths at a temperature ranging from room temperature (25° C.) to 100° C. Washing is typically carried out with baths in a temperature in the range of 50 to 70° C. When performed, it is preferable to wash the aluminium oxide prior to further processing the aluminium oxide with the soluble metal and other components. Alternatively, it is also possible to perform washing for removal of impurities after processing the aluminium oxide with the other components described below, but before forming a spinel phase.

Metal Capable of Forming Spinel Phase

Generally, suitable metal compounds capable of forming a spinel phase are those metal compounds capable of forming a metal aluminate spinel, and therefore include those divalent (+2) metals.

Suitable metals include, but are not limited to, those +2 valence metals listed in Group IIA of the periodic table including beryllium, magnesium, calcium, strontium, barium and radium, those of Group IIB of the periodic table including zinc, cadmium and mercury and transition metals including chromium, manganese, iron, cobalt, nickel and copper. Particularly suitable metals include, zinc and/or nickel.

The metal compound chosen above acts to form spinel phase once it is combined and processed with the aluminium oxide described below.

Suitable compounds containing the metal are soluble in the medium employed to combine and mix the metal source with aluminium oxide and the trivalent aluminium compound described below. The metal compound is preferably a salt form derived from either mineral acids, or organic acids, with nitrate, chloride, and acetate salts being particularly suitable for aqueous based mediums. Notwithstanding, the components, including the spinel forming metal compound, can be combined in organic solvents such as acetone, methanol, ethanol, dimethyl formamide, diethyl ether, cyclohexane, xylene, and tetrahydrofuran.

Soluble Trivalent Aluminium Compound

The soluble Al$^{3+}$ compound is one that is soluble in the medium chosen to combine and mix the aforementioned components, and should be in a form that, when mixed with the other components, does not cause significant gelling, e.g., reacts with the above components or interacts with the mixing medium. Choosing a soluble compound, compared to, e.g., solid particulate binders, enhances the ability of the compound to intimately mix it with the other components. The compound can therefore vary depending on the desired properties of the final support and the properties of the components selected to form the metal aluminate spinel. Ionic compounds containing trivalent Al are particularly suitable, and include aluminium nitrate, aluminium chlorohydrol, aluminium chloride, aluminium sulphate. Such ionic compounds can be very effective in binding particles which are non-peptizable, but possess desirable physical properties (e.g. surface area, pore volume, and crystallite size).

A particularly suitable soluble trivalent Al compound is aluminium nitrate, although aluminium sulphate, aluminium chloride can be used as effectively. Typical loading of the compound is in the range of 2 to 20 wt %, and will typically be around 10 wt % on a total aluminium oxide basis in the mixture. Lower loadings of 5% are also effective, with amounts as low as 3% or less possible with a combination of mineral or organic acid additives, and the solids content is such that gelling is not likely to occur.

Without being held to a particular theory, it is believed the soluble Al$^{3+}$ compound is a binder precursor that serves to form a binder in the metal aluminate spinel composition because its addition to the other two components serves to enhance the final composition's attrition. The solubility of the compound permits extensive dispersion and contact with the aluminium oxide when being mixed, as well as contact with the spinel as the spinel phase is formed. Once the subsequent processing is completed, e.g., dried and then calcined, to form a final support with a spinel phase, it is believed that the aluminium nitrate has converted (e.g., been decomposed) to an alumina species that binds the metal aluminate spinel phase (and any transition alumina or other chemical species present) to form an attrition resistant catalyst support.

It is envisaged that other components can be included in the process to act as a binder for the aluminate spinel composition. It should be understood that the description should not be construed to mean that all of the trivalent aluminium compound acts as, or converts to a binder.

The aluminium oxide, the metal compound capable of forming a spinel phase, and the soluble trivalent aluminium compound are added to a suitable medium at room temperature that can be later mixed, preferably under intimate mixing conditions, and processed to reduce particle size of solids present. The components can be added in any order, at a temperature in a range of 0 to 100° C. It is preferable that the temperature is sufficient for the soluble components (spinel forming metal source and trivalent aluminium) to be dissolved in the medium. As mentioned above, the medium can be aqueous or other media such as the organic media mentioned earlier can be used. In an embodiment which the aluminium oxide comprises gamma alumina prepared from calcination of boehmite, the soluble components can be directly added to an aqueous slurry of the gamma alumina, after calcining the boehmite alumina.

The relative weight proportions added to the medium typically are in the range of 65 to 95 wt % as aluminium oxide, 2 to 20 wt % as spinel forming metal oxide and 3 to 15 wt % Al$^{3+}$ as oxide.

The pH of the medium containing the three components is preferably less than 5.

Each of the aluminium oxide component and the spinel forming metal components may comprise two or more species of the component. For example, a mixture of two different aluminium oxides, and/or a mixture of two different spinel forming metal compounds may be employed to produce a spinel phase comprising two different metal aluminate spinels. While not typical, it may be desirable to employ two or more different soluble trivalent aluminium compounds.

There may also be included optional components in addition to these three components. These optional components include textural promoters, e.g., lanthana, silica, clay, phosphorus, and the like.

Mixing

Once combined in an appropriate medium, the aluminium oxide, spinel forming metal compound, and trivalent aluminium compound are mixed under conditions sufficient to disperse the components preferably under conditions sufficient to form a slurry. In some embodiments, the components are mixed into a well dispersed slurry in order to maximize contact of the components with one another. A "well dispersed slurry" can be defined in this context as one in which the solids in the slurry, do not readily settle and would for example stay in dispersion for at least fifteen minutes to an hour before a significant portion of the solids settles. The dispersion can be carried out at room temperature or higher, e.g. room temperature to 100° C. The mixing is carried out so that the components are intimately mixed and can be conducted in a conventional mixer. Without being held to a particular theory, it is believed that by forming a slurry of the aluminium oxide and spinel forming metal compound, one can add other components such as the soluble compound of a trivalent aluminium, and create a medium that is more readily conducive to reactions and/or the interaction if the spinel forming components, with the additional components.

The mixing is also conducted under conditions such that no significant gelling occurs, while at the same time achieve a mixture having relatively high solids going into the processing steps that form the catalyst support and convert the mixture to a metal aluminate spinel phase composition. Indeed, as mentioned above, it is possible and desirable to produce a mixture having at least 20% by weight solids, and more desirable to attain about 25 to 30% solids. Such solids levels are especially achievable when selecting a calcined alumina as the aluminium oxide. It has been shown that gamma alumina produced from calcining boehmite alumina provides a high solids slurry during mixing. It is believed that higher solids tend to produce a more attrition resistant support, and with minimum gelling, the process effectively disperses the trivalent aluminium and results in a less viscous feed to a dryer.

Once the components are mixed, the particle size of the solids, e.g. aluminium oxide, can be reduced to a median particle size below 10 microns, preferably in a range of 1 to 5 microns. Indeed, the mixing and particle size reduction can be simultaneously carried out in a high energy mechanical mill, typically a mill such as a ball mill, a media mill, or a continuous mill such as a DRAIS continuous mill. The particle size reduction can be carried out at room temperature, although the medium containing the components can attain higher temperatures during particle size reduction, e.g. milling. It is frequently desirable to mix the components simultaneously to form a slurry and reduce the solids particle size to a size below 10 microns, and preferably to a size in the range of 1 to 5 microns. It is also preferable that simultaneous mixing and particle size reduction should be conducted under conditions such that no significant gelling occurs, while at the same time, achieving a mixture having a relatively high solids content going into the processing steps that form the catalyst support and convert the mixture to a metal aluminate spinel phase.

Processing to Metal Aluminate Spinel Phase

The mixture of aluminium oxide, spinel forming metal compound and trivalent aluminium compound described above is then processed to form the metal aluminate spinel composition. This can be achieved through subjecting the mixture to a calcination temperature sufficient to produce a metal aluminate spinel phase. This can be attained by calcination, typically carried out in a furnace (either continuous rotary type or stationary type) at a temperature in the range of 700 to 1300° C.

The mixture is generally fed to, or otherwise introduced to, a dryer prior to spinel phase formation, preferably a spray dryer, to remove the liquid medium, and to form a particulate having a size sufficient to serve as a support for FT catalysts. When utilizing a spray dryer, the inlet temperature of the dryer can be set at a temperature in the range of 100 to 400° C., and an outlet temperature in the range of 100 to 200° C. It is desirable that particles recovered from the spray dryer have a median particle size in the range of 20 to 100 microns.

The proportion of the overall composition represented by the spinel phase to some degree depends on the relative amounts of the spinel forming metal and the aluminium oxide added, but also depends on the temperatures used to process the composition and the amounts of other components added to the mixture prior to processing.

Once calcined, the support particles from this process typically have an attrition resistance value of less than 10%, more commonly, less than 5%. This attrition resistance value refers to a modified ASTM 5757 method, and is measured as follows:

The equipment consists of two main parts, one air feeding system and one reactor where the attrition takes place. Compressed air passes through a pressure regulator (5 bar) to a moisture chamber where the air is moistened to approximately 30% relative moisture. This is done to avoid static electricity in the system. The amount of air is then adjusted in a mass flow controller. The humid air then enters the reactor through a sieve tray where the holes have a diameter of 0.4 mm. Because of these holes, the gas reaches sonic velocity, which causes the "wear and tear" on the particles in the reactor.

Reactors used for this testing are known in the art. Typically, the reactor has an internal diameter of 35.6 mm (1.4 inches) and a length of 711 mm (28 inches) and the pressure is approximately 1.8 bar. After passing through the reactor, the velocity is lowered in a separation chamber which has an internal diameter of 112 mm (4.4 inches) and a length of 305 mm (12 inches). There is a conical connection 203 mm (8 inches) between the reactor and the separation chamber.

Particles >40 μm will fall back into the reactor, while smaller particles <40 μm will enter a soxhlet-filter through a u-formed tubing, connected to the separation chamber via a conical connection 106 mm long (4 inches). A vibrator is mounted on the separation chamber, to loosen any particles on the inside walls.

50 g of powder or catalyst, sieved to >40 μm before testing, is loaded to the reactor, and the reactor is connected to the separation chamber. The air is turned on, and the fines produced in the reactor and collected in the soxhlet filter are weighed at given time intervals. A normal run lasts 5 hours and the amount of fines produced can be plotted against time. The test is typically run for five hours using a 50 g test sample of particles sieved to greater than 40 microns. The attrition resistance value is calculated as percent particles <40 μm generated after 5 hours.

It has also been shown that the process of this invention is capable of providing supports with a metal aluminate spinel phase with an attrition resistance value 5% or less, even at after calcining at a temperature in the range of 700 to 1050° C., whereas previously, such attrition resistance values were only seen for supports with a metal aluminate spinel phase after calcination at temperatures greater than 1100° C. and approaching 1300° C.

It is also possible to measure attrition resistance using a Davison Index (DI) method. In this method the particle size of the calcined metal aluminate spinel composition is measured using a standard particle size analyzer such as a MALVERN mastersizer. The fraction of particles less than 20 microns is noted. A 7.0 gram sample of the same support is subjected to a 20 minute attrition in a standard hardened steel jet cup having a precision bored orifice. An air flow of 21 liters a minute is used. The particle size after attrition is measured again and the fraction less than 20 microns is noted. The Davison Index is calculated as follows $$\text{Davison Index} = \frac{\text{Fraction of particles less than 20 microns (Before attrition} - \text{After attrition)}}{\text{Fraction of particles less than 20 microns before attrition}}$$

The composition of the preferred support material comprises a metal aluminate spinel phase as can be evidenced by x-ray diffraction (XRD). The metal aluminate spinel peaks in a XRD pattern can usually be seen for compositions heated to at least 700° C., the temperature at which one typically first sees formation of the spinel phase. These peaks become sharper for compositions heated at higher temperatures along the range of 700 to 1300° C. The composition may also comprise an alumina phase, primarily alpha alumina, depending on the starting aluminium oxide, the amount of the spinel forming metal compound present, and the temperature at which the mixture is processed. Varying amounts of other transition phase alumina may also be present, again depending on the starting aluminium oxide, and the temperature at which the mixture is processed. In some embodiments, converting all reactive alumina in the starting aluminium oxide, or otherwise produced during processing, to alpha alumina may be desirable in order to reduce reactive surfaces capable of deactivating catalyst metal species added later when processing the support to a finished catalyst. These embodiments would therefore require calcination temperatures of at least 1000° C., the temperature above which gamma alumina transitions to alpha alumina. In other embodiments, it may be desirable to maintain some level of higher surface area and higher pore volume alumina, e.g., gamma alumina, in order to provide either more surface area for greater dispersion of catalytic species or more pore volume for higher loading of catalytically active metal species. It is therefore possible to choose lower calcination temperatures to ensure a larger amount of gamma, and at the same time produce an attrition resistant support at lower temperatures.

The present invention allows for flexibility in selecting particular features for a support. For example, calcining the mixture to a temperature in the range of 900 to 1300° C. enables an attrition resistance support to be obtained which has increasing amounts of alpha alumina as 1300° C. is approached, thereby likely increasing the life of the catalyst utilizing the support because there is less alumina surface capable of deactivating the catalytic metal. On the other hand, calcining the mixture to a temperature in the range of 700 to 900° C., still results in an attrition resistant support, but with higher surface area and higher pore volume because the support will contain larger amounts of higher surface transition alumina (other than alpha alumina). Indeed, it may be desirable to calcine the mixture at a temperature in the range of 950 to 1050° C. to attain a balance of features from both of the previous two variants.

FT Catalyst

Once the catalyst support with spinel phase is formed, it can then be processed to include catalytic metal species suitable for catalysis of FT synthesis. Such metals include catalytic metal selected from among the Group 8 elements of the Periodic Table, such as iron (Fe), ruthenium (Ru), and osmium (Os); Group 9 elements, such as cobalt (Co), rhodium (Rh), and iridium (Ir); Group 10 elements, such as nickel (Ni), palladium (Pd), and platinum (Pt); and the metals molybdenum (Mo), rhenium (Re), and tungsten (W). The catalytic metal more preferably comprises cobalt, iron, ruthenium, nickel, or combinations thereof. The catalytic metal still more preferably comprises cobalt, iron, ruthenium, or combinations thereof. Most preferably, the catalytic metal comprises cobalt.

The amount of catalytic metal present in the catalyst may vary widely. When the catalytic metal is cobalt, the catalyst may have cobalt in an amount totaling from about 1% to about 50% by weight (as the metal) of total catalyst composition (catalytic metal, support, and any optional promoters), more preferably from about 5% to about 40% by weight, still more preferably from about 7 to about 37% by weight, and most preferably from about 10 to about 30% by weight. An iron containing catalyst however may comprise about 5 to about 75 wt. % iron, preferably from about 10 to about 60 wt. % iron, more preferably from about 20 to about 50 wt. % iron. Ruthenium catalyst can comprise about 0.01 to about 5 wt. % ruthenium, preferably from about 0.5 to about 4 wt. % ruthenium, more preferably from about 1 to about 3 wt. % ruthenium.

Catalysts prepared using the preferred support may also comprise promoters. The promoter may vary according to the catalytic metal. A promoter can be an element that also, in an active form, has catalytic activity in the absence of the catalytic metal. Such an element is considered a promoter when it is present in the catalyst in a lower wt % than the catalytic metal, and it enhances the performance of the catalyst in FT synthesis. Suitable measures of the performance that may be enhanced include selectivity, activity, stability, lifetime, reducibility and resistance to potential poisoning by impurities such as sulfur, nitrogen, and oxygen.

Suitable promoters vary with the catalytic metal and can be selected from Groups 1-15 of the Periodic Table of the Elements. A promoter can be in elemental form. Alternatively, a promoter can be present in an oxide compound. Further, a promoter can be present in an alloy containing the catalytic metal. Except as otherwise specified herein, a promoter is preferably present in an amount to provide a weight ratio of elemental promoter:elemental catalytic metal of from about 0.00005:1 to about 0.5:1, preferably from about 0.0005:1 to about 0.25:1 (dry basis). When the promoter comprises a metal from Groups 7, 8, 9, and 10 of the Periodic Table such as rhenium, ruthenium, platinum, or palladium, the weight ratio of elemental promoter:elemental catalytic metal may be between about 0.00005:1 and about 0.05:1.

A catalyst comprising the preferred support can be prepared using various techniques. Without limitation, examples of suitable methods include impregnating a catalyst material onto the support of the present invention, extruding the stabilized support together with the catalyst material to prepare catalyst extrudates, spray-drying the catalyst material and the support from a solution containing both, and/or precipitating the catalyst material onto a support. The supported catalysts may be used in the form of powders, particles, pellets, monoliths, honeycombs, packed beds, foams, and aerogels. The catalyst material can include any one or any combination of a catalytic metal, a precursor compound of a catalytic metal, a promoter, and a precursor compound of a promoter. The most preferred method of preparation may depend, for example, on the desired catalyst particle size.

The preferred support for the catalyst of this the present invention addresses several issues exhibited by prior supports and their methods of manufacture. It is appreciated that metal aluminate spinel has a lower propensity for reaction with catalytically the active metal added to the support. However, the preferred support adds additional benefits by providing a binding component and processing step compatible with the process of producing a spinel composition such that the attrition problem associated with spinels that have not been calcined are overcome. The process further provides an attrition resistant spinel composition at more moderate temperatures and lower metal content compared to calcined attrition resistant spinel phase containing supports known in the art, which in turn reduces the expense of manufacturing the support, while also providing the manufacturer with a wider range of options in equipment the manufacturer uses. For example, if a manufacturer decides to calcine a metal aluminate spinel composition at high temperature to attain attrition resistance, the manufacturer has to select particular equipment capable of handling high temperatures. Highly calcined metal aluminate spinel phases unfavorably interact, e.g., adhere, with the processing equipment's metal surfaces (e.g., stainless steel) at very high temperatures.

To further illustrate the present invention and its advantages, the following specific examples are given. The examples are given as specific illustrations of the claimed invention. It should be understood, however, that the invention is not limited to the specific details set forth in the examples.

All parts and percentages in the examples, as well as the remainder of the specification, which refers to solid compositions or concentrations, are by weight unless otherwise specified. However, all parts and percentages in the examples as well as the remainder of the specification referring to gas compositions are molar or by volume unless otherwise specified.

EXAMPLES

Modified Aluminium Oxide Support Preparation

Comparative Examples 1 and 2

In these examples gamma-alumina is modified by metal salt impregnation and high temperature calcination to achieve materials that have stronger resistance to attrition and abrasion in a slurry environment, as described by Rytter et. al (WO 2005/072866). These materials were prepared by one-step incipient wetness impregnation of aqueous solutions of nickel- or zinc nitrate hexahydrate to obtain nominal amounts of 15% zinc and 10% nickel. The technique is the same as described earlier for preparing catalysts. The impregnated materials were dried for 3 h at a temperature of 110° C. During drying, the materials were stirred every 15 min during the first hour and every 30 min during the next two hours. After impregnation and drying, the samples were calcined at 1140° C. for 16 h.

Examples 3 to 9

In these examples, the method of the invention is used to prepare modified aluminium oxide materials with stronger resistance to attrition and abrasion. Details of preparation for the material of Example 3 is as follows:

A commercial pseudo boehmite such as Pural SB from Sasol (called Pural 1 in Table 1) was first calcined at approximately 550° C. to yield γ-alumina. Separately, 14 kg of DI water was weighed in a drum to which e.g. 6 kg of aluminium nitrate (13.6% alumina) was added. About 7.5 kg of calcined alumina described above was added to the mixture of water and Al-nitrate solution with constant agitation. Finally, e.g. 1.64 kg of a commercially available Zn-nitrate solution (22.8% ZnO) was added to the above mixture. An intimate contact of alumina, binder and divalent metal nitrate (Zn-nitrate) was obtained in a high energy mechanical mill. The resulting milled particle size was around 1.5 microns. The milled slurry was dried in a spray dryer with an outlet temperature of around 120° C. to obtain microspheroidal support particles. A portion of the microspheres was calcined in an oven at 900° C. for 4 hours to obtain Zn-aluminate support. Ni-aluminate support was prepared in the same manner, but using Ni-nitrate crystals (GFS chemicals, 25.7% NiO) instead of Zn-nitrate.

The other modified aluminium oxide materials in Example 4-9 given in Table 1 were obtained by changing the amount of dopant (zinc nitrate or nickel nitrate) and calcination temperature.

Catalyst Preparation

Examples 1 to 9

The catalysts of Examples 1-9 contain a normal amount of 12 wt % Co, 0.5 wt % Re, as calculated assuming reduced catalysts with complete reduction of cobalt. The actual metal loading as determined by XRF or ICP may vary by up to 10%, e.g. for a catalyst with nominal loading of 12 wt %, the actual amount of cobalt can vary between 10.8 and 13.2 wt % of the total reduced catalyst weight. The catalysts were prepared by one-step incipient wetness co-impregnation of different nickel- or zincaluminate supports with aqueous solutions of cobalt nitrate hexahydrate and perrhenic acid. The freshly prepared catalysts were dried for 3 h at a temperature of 110° C. During drying, the catalysts were stirred every 15 min during the first hour and every 30 min during the next two hours. After impregnation and drying, the samples were calcined at 300° C. for 16 h.

Catalyst Testing

The fixed bed testing was performed in a laboratory unit with four parallel fixed-bed reactors. 1.7 g of catalyst particles in a size fraction between 53 and 90 microns was mixed with 20 g of inert SiC. Reduction was performed in situ at 350° C. for 16 h in hydrogen before a mixture of hydrogen and CO at ratio 2:1 was added. After 20 h on stream at 210° C. and 20 bar total pressure, the space velocity was adjusted to give an estimated conversion level of CO between 45 and 50% after 100 h. It is very important to perform selectivity, as well as activity, comparisons at the same level of conversion, as the level of steam generated in the reaction has a profound influence on the catalyst performance.

Results

TABLE 1

| | | | | All catalysts have 12% Co and 0.5 Re. | | | | |
|---|---|---|---|---|---|---|---|---|
| Example No. | Alumina* | Alumina** SA/PV*** | Spinel forming metal compound | Tcalc1 (° C.) | Aluminate SA/PV* | Attrition (%) | RA | Rel C5+ |
| 1 (comp.) | Pural 2 | 170/0.73 | 15% ZnO | 1140 | 13/0.15 | 6.8 | 0.67 | 0.981 |
| 2 (comp.) | Pural 2 | 170/0.73 | 10% NiO | 1140 | 18/0.17 | 3.0 | 0.78 | 0.973 |

TABLE 1-continued

All catalysts have 12% Co and 0.5 Re.

| Example No. | Alumina* | Alumina** SA/PV*** | Spinel forming metal compound | Tcalc1 (° C.) | Aluminate SA/PV* | Attrition (%) | RA | Rel C5+ |
|---|---|---|---|---|---|---|---|---|
| 3 | Pural 1 | 190/0.51 | 4.5% NiO | 600 | 178/0.28 | 1.73 | 0.54 | 0.878 |
| 4 | Pural 1 | 190/0.51 | 4.5% NiO | 1000 | 85/0.24 | 0.98 | 0.53 | 0.906 |
| 5 | Pural 2 | 170/0.73 | 8% ZnO | 1000 | 46/0.23 | 2.3 | 0.82 | 0.951 |
| 6 | Pural 3 | 160/0.84 | 8% ZnO | 1000 | 76/0.41 | 3.3 | 0.85 | 0.932 |
| 7 | Pural 2 | 170/0.73 | 5% ZnO | 1000 | 40/0.22 | 0.9 | 0.89 | 0.950 |
| 8 | Pural 3 | 160/0.84 | 4.9% ZnO | 1000 | 72/0.40 | 3.1 | 0.87 | 0.922 |
| 9 | Pural 2 | 170/0.73 | 5% ZnO | 900 | 93/0.24 | 1.2 | 0.85 | 0.922 |

*Pseudo-boehmite alumina.
**Pseudo-boehmite alumina calcined to 550° C.
***Surface area (SA) given in m$^2$/g and pore volume (PV) given in cm$^3$/g.

The results given in Table 1 show that the catalysts of the present invention have good Fischer-Tropsch activities and attrition resistances comparable or better than those of Examples 1 and 2. The results demonstrate the manufacture of modified support materials achieved at much lower temperatures than previously known in the art, providing the manufacturer a wider range of options in equipment. In particular, the benefit of lower temperatures needed for achieving the same resistance to attrition is of great importance.

The present invention has been described with reference to the presently preferred embodiments thereof. It is not intended that the present invention be limited by the preferred embodiments. Instead, it is intended that the present invention be defined by the following claims.

The invention claimed is:

1. A method of producing a modified aluminium oxide supported catalyst, the method comprising the steps of:
    forming a slurry by mixing aluminium oxide, a 2-valent metal compound capable of forming a spinel phase, and a soluble compound of trivalent aluminium;
    shaping a solid material from the slurry into a solid precursor material;
    calcining the precursor material at a temperature in the range of 700° C. to 1300° C. to produce a modified aluminium oxide support material including a metal aluminate spinel phase compound formed by the metal capable of forming a spinel phase and the aluminium oxide;
    impregnating the modified aluminium oxide support material with a source of cobalt to form an impregnated modified aluminium oxide support material; and
    calcining the impregnated modified aluminium oxide support material at a temperature of at least 150° C. to produce the modified aluminium oxide supported catalyst.

2. The method of claim 1, wherein the aluminium oxide is selected from the group consisting of gamma alumina, delta alumina, theta alumina, eta alumina, rho alumina, and mixtures thereof.

3. The method of claim 2, wherein the aluminium oxide predominantly comprises gamma alumina.

4. The method of claim 3, wherein the gamma alumina is prepared by heating boehmite alumina at a temperature sufficient to convert boehmite alumina to gamma alumina.

5. The method of claim 4, wherein the boehmite alumina is heated to a temperature in the range of 400° C. to 700° C.

6. The method of claim 1, wherein the spinel forming metal compound is selected from compounds of cobalt, zinc, copper, magnesium, calcium, manganese, nickel, iron, and mixtures thereof.

7. The method of claim 6, wherein the spinel forming metal compound is a soluble metal salt selected from the group consisting of zinc nitrate, nickel nitrate, and magnesium nitrate.

8. The method of claim 1, wherein the amount of spinel forming metal compound added is in the range of 1 to 50 wt %, expressed as the wt % of the spinel forming metal based on the total weight of modified support.

9. The method of claim 1, wherein the soluble compound of trivalent aluminium is selected from the group consisting of aluminium nitrate, aluminium chlorohydrol, aluminium sulphate, aluminium chloride, aluminium acetate, aluminium formate, and mixtures thereof.

10. The method of claim 1, wherein mixing the slurry reduces the particle size of solids in the mixture to a median particle size that is less than ten microns.

11. The method of claim 10, wherein the mixing is without significant gelling.

12. The method of claim 10, wherein the mixing is conducted in a mill.

13. The method of claim 10, wherein the mixing reduces the particle size of solids in the mixture to a median particle size in the range of 1 to 5 microns.

14. The method of claim 1, wherein the shaping step comprises drying the said material at a temperature in the range of 100 to 400° C. to form particles having a median particle size in the range of 20 to 100 microns.

15. The method of claim 14, wherein the drying is carried out in a spray drier.

16. The method of claim 1, wherein the forming step is selected from the group consisting of spray-drying, peletization and extrusion.

17. The method of claim 1, further comprising washing the solid material before the shaping step.

18. The method of claim 17, wherein the washing step is performed with water containing less than 300 ppm calcium and/or less than 300 ppm sodium.

19. The method of claim 1, wherein the calcining the precursor material step is carried out at a temperature in the range of 700 to 1050° C.

20. The method of claim 19, wherein product from the calcining the precursor material step, further comprises alpha alumina.

21. The method of claim 1, wherein the calcining the precursor material step is carried out in several calcination steps, each of which covers a part of the temperature range up to the maximum temperature.

22. The method of claim 1, wherein the modified aluminium oxide support is produced by: combining aluminium oxide selected from the group consisting of gamma alumina, delta alumina, theta alumina, eta alumina, rho alumina and mixtures thereof, a 2-valent soluble compound of spinel forming metal or mixture of metals, and a soluble compound of trivalent aluminium selected from the group consisting of aluminium nitrate, aluminium chlorohydol, aluminium sulphate, aluminium chloride and mixtures thereof; reducing the particle size of the solids in the mixture to a median particle size of less than ten microns; drying the mixture at a temperature in the range of 100 to 400° C.; and calcining the dried mixture at a temperature in the range of 700 to 1300° C.

23. The method of claim 22, wherein the particle size of solids in the mixture is reduced to a median particle size in the range of 1 to 5 microns, the mixture is dried at a temperature in the range of 100 to 400° C., and the dried mixture is calcined at a temperature in the range of 700 to 1050° C.

24. The method of claim 23, wherein the aluminium oxide is gamma alumina, the compound of spinel forming metal is a metal nitrate salt and the trivalent aluminium is aluminium nitrate.

25. The method of claim 24, further comprising drying the mixture at a temperature in the range of 100 to 400° C. to form particles having a median particle size in the range of 20 to 100 microns prior to the step of calcining the precursor material.

26. The method of claim 1, wherein the support material is porous, the porous support material is modified by treatment with a divalent metal, the source of catalytically active metal is cobalt, and prior to the cobalt impregnation step, the modified support material has a specific surface area in the range of 30 to 80 m$^2$/g.

27. The method of claim 26, wherein the porous support material is modified by treatment with a divalent metal and prior to the cobalt impregnation step, the modified support material has a pore volume below 0.5 ml/g.

28. The method of claim 1, wherein the impregnation step comprises an incipient wetness treatment wherein an aqueous solution of the catalytically active metal is mixed with the modified support material until the pores are filled and the impregnated modified support material is then dried, prior to the step of calcining the impregnated modified aluminium oxide support material.

29. The method of claim 28, wherein the amount of aqueous solution used in the impregnation is 0.05 to 2 times larger than the measured pore volume of the catalyst support.

30. The method of claim 29, wherein the drying is carried out at 80 to 120° C.

31. The method of claim 1, wherein the source of cobalt is selected from the group consisting of cobalt nitrate (Co(NO$_3$)$_2$), cobalt acetate(s), cobalt halide(s), cobalt (hexa) amine salt(s) and organic cobalt compounds.

32. The method of claim 31, wherein after the impregnation step, the cobalt content of the impregnated modified support material is in the range of 3 to 60 wt %, measured as the metal weight of the total catalyst after reduction.

33. The method of claim 1, wherein the impregnated modified support material is calcined at a temperature of up to 600° C. in the step of calcining the impregnated modified aluminium oxide support material.

34. The method of claim 1, further comprising activating the supported catalyst material after the step of calcining the impregnated modified aluminium oxide support material.

35. The method of claim 34, wherein the activation step comprises reduction of a substantial portion of the catalytically active metal compound present to the metal.

36. The method of claim 35, wherein the reduction is carried out by treating the catalyst material with a reducing gas.

37. The method of claim 36, wherein the reducing gas is selected from the group consisting of hydrogen, carbon monoxide and a mixture thereof.

38. The method of claim 35, wherein the reduction is carried out at an activation temperature in the range 20 to 500° C.

39. The method of claim 1, wherein prior to the impregnation step, the modified support has an ASTM attrition value of less than 5%.

40. A catalyst material produced by the method of claim 1, wherein the catalyst material comprises a support derived from aluminium oxide in the presence of a soluble compound of trivalent aluminium, the aluminium oxide being modified by the presence of a spinel phase formed from the aluminium oxide and spinel-forming 2-valent metal, and impregnated with a source of cobalt.

41. The catalyst of claim 40, wherein the spinel phase is substantially homogeneously distributed throughout the aluminium oxide and the cobalt is absorbed or adsorbed on to the surface of the modified support.

42. The catalyst of claim 40, wherein the spinel forming 2-valent metal is nickel.

43. The catalyst of claim 40, wherein the cobalt content of the catalyst is from 8 to 18% by weight.

44. The catalyst of claim 40, wherein the catalyst material comprises less than 3% by weight of a promoter.

45. The catalyst of claim 44, wherein the promoter is selected from rhenium and platinum.

46. A method for the production of hydrocarbons, comprising:
forming a slurry by mixing aluminium oxide, a 2-valent metal compound capable of forming a spinel phase, and a soluble compound of trivalent aluminium;
shaping a solid material from the slurry into a solid precursor material;
calcining the precursor material at a temperature in the range of 700° C. to 1300° C. to produce a modified aluminium oxide support material including a metal aluminate spinel phase compound formed by the metal capable of forming a spinel phase and the aluminium oxide;
impregnating the modified aluminium oxide support material with a source of cobalt to produce an impregnated modified aluminium oxide support material;
calcining the impregnated modified aluminium oxide support material at a temperature of at least 150° C. to produce the modified aluminium oxide supported catalyst; and
subjecting H$_2$ and CO gases to a Fischer-Tropsch synthesis reaction in a reactor in the presence of the modified aluminium oxide supported catalyst.

47. The method of claim 46, wherein the reactor is a three-phase reactor in which the reactants are gaseous, the product is at least partially liquid and the modified aluminium oxide supported catalyst is solid.

48. The method of claim 47, wherein the reaction is carried out in a slurry bubble column reactor.

49. The method of claim 48, wherein the $H_2$ and CO are supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry.

50. The method of claim 49, wherein the reaction temperature is in the range 190-280° C.

51. The method of claim 50, wherein the reaction temperature is in the range 210-250° C.

52. The method of claim 51, wherein the reaction pressure is in the range 10 to 60 bar.

53. The method of claim 52, wherein the reaction pressure is in the range 15 to 35 bar.

54. The method of claim 49, wherein a $H_2$/CO ratio of the gases supplied to the Fischer-Tropsch synthesis reactor is in the range 1.1 to 2.2.

55. The method of claim 54, wherein the $H_2$/CO ratio is in the range 1.5 to 1.95.

56. The method of claim 49, wherein a superficial gas velocity in the reactor is in the range 5 to 60 cm/s.

57. The method of claim 56, wherein the superficial gas velocity is in the range 20 to 40 cm/s.

58. The method of claim 49, further comprising subjecting the product of the Fischer-Tropsch synthesis reaction to post-processing.

59. The method of claim 58, wherein the post-processing is selected from de-waxing, hydro-isomerization, hydro-cracking, and combinations thereof.

60. A method of producing a modified aluminium oxide supported catalyst, the method comprising the steps of:
   forming a slurry by mixing aluminium oxide, a metal compound capable of forming a spinel phase, and a soluble compound of trivalent aluminium, wherein solids within the slurry have a mean particle size that is less than ten microns;
   shaping a solid material from the slurry into a solid precursor material;
   calcining the precursor material at a temperature of at least 700° C. to produce a modified aluminium oxide support material including a metal aluminate spinel phase compound formed by the metal capable of forming a spinel phase and the aluminium oxide;
   impregnating the modified aluminium oxide support material with a source of catalytically active metal to form an impregnated modified aluminium oxide support material; and
   calcining the impregnated modified aluminium oxide support material at a temperature of at least 150° C. to produce the modified aluminium oxide supported catalyst.

61. A method of producing a modified aluminium oxide supported catalyst, the method comprising the steps of:
   forming a slurry by mixing aluminium oxide, a 2-valent soluble compound of spinel forming metal or mixture of metals capable of forming a spinel phase, and a soluble compound of trivalent aluminum such that a median particle size of solids within the slurry is less than ten microns, wherein the aluminum oxide is selected from the group consisting of gamma alumina, delta alumina, theta alumina, eta alumina, rho alumina and mixtures thereof and wherein the soluble compound of trivalent aluminium is selected from the group consisting of aluminium nitrate, aluminium chlorohydol, aluminium sulphate, aluminium chloride and mixtures thereof;
   drying the slurry at a temperature in the range of 100° C. to 400° C.;
   shaping a solid material from the slurry into a solid precursor material;
   calcining the precursor material at a temperature in the range of 700° C. to 1300° C. to produce a modified aluminium oxide support material including a metal aluminate spinel phase compound formed by the metal capable of forming a spinel phase and the aluminium oxide;
   impregnating the modified aluminium oxide support material with a source of catalytically active metal to form an impregnated modified aluminium oxide support material; and
   calcining the impregnated modified aluminium oxide support material at a temperature of at least 150° C. to produce the modified aluminium oxide supported catalyst.

* * * * *